(12) United States Patent
Crawford et al.

(10) Patent No.: US 12,369,776 B2
(45) Date of Patent: Jul. 29, 2025

(54) DEVICES, SYSTEMS, AND METHODS FOR AN INSTRUMENT ACCESSORY

(71) Applicant: Boston Scientific Scimed, Inc., Maple Grove, MN (US)

(72) Inventors: Richard Crawford, Galway (IE); Méabh Holden, Dublin (IE); Enda Connaughton, Galway (IE); Martin L Fawdry, Galway (IE)

(73) Assignee: Boston Scientific Scimed, Inc., Maple Grove, MN (US)

(*) Notice: Subject to any disclaimer, the term of this patent is extended or adjusted under 35 U.S.C. 154(b) by 48 days.

(21) Appl. No.: 17/165,524

(22) Filed: Feb. 2, 2021

(65) Prior Publication Data
US 2021/0235971 A1    Aug. 5, 2021

Related U.S. Application Data

(60) Provisional application No. 62/969,922, filed on Feb. 4, 2020.

(51) Int. Cl.
*A61B 1/00* (2006.01)
*A61B 1/31* (2006.01)

(52) U.S. Cl.
CPC ...... *A61B 1/00135* (2013.01); *A61B 1/00064* (2013.01); *A61B 1/00137* (2013.01);
(Continued)

(58) Field of Classification Search
CPC ............ A61B 1/00135; A61B 1/00137; A61B 1/00064; A61B 1/00154; A61B 1/31;
(Continued)

(56) References Cited

U.S. PATENT DOCUMENTS

| 3,797,478 A | * | 3/1974 | Walsh | ................... | A61F 2/0027 |
| | | | | | 128/DIG. 25 |
| 4,315,509 A | | 2/1982 | Smit | | |

(Continued)

FOREIGN PATENT DOCUMENTS

JP    2006-500970 A    1/2001
JP    2001-527448 A    12/2001
(Continued)

OTHER PUBLICATIONS

International Search Report and Written Opinion for the International Patent Application No. PCT/US2021/016217, mailed Apr. 12, 2021, 16 pages.

(Continued)

*Primary Examiner* — Ryan N Henderson
(74) *Attorney, Agent, or Firm* — Seager, Tufte & Wickhem, LLP

(57) ABSTRACT

The present disclosure, in its various aspects, is directed to instrument accessory devices, implementation methods, and related delivery systems. Embodiments according to the present disclosure, including as described herein, may increase the effectiveness and efficiency of endoscopic procedures, such as Endoscopic Retrograde Cholangiopancreatography (ERCP). In one example, an embodiment includes an instrument accessory device with an expandable member, the device configured to receive an instrument through an instrument lumen, wherein the outer surface may comprise an expandable material. The device may comprise a constrainment element disposed about the outer surface of the expandable member, the constrainment element comprising a proximal end, a distal end, an inner surface, and an outer surface.

15 Claims, 6 Drawing Sheets

(52) U.S. Cl.
CPC .......... *A61B 1/00154* (2013.01); *A61B 1/31* (2013.01); *A61B 2217/007* (2013.01)

(58) Field of Classification Search
CPC .............. A61B 1/00082; A61M 25/10; A61M 25/1011; A61M 2025/1081; A61M 2025/1084; A61M 2025/1013
See application file for complete search history.

(56) References Cited

U.S. PATENT DOCUMENTS

| | | | |
|---|---|---|---|
| 5,620,408 A | 4/1997 | Vennes et al. | |
| 5,662,588 A * | 9/1997 | Lida ................... | A61B 1/00091 600/125 |
| 5,904,701 A * | 5/1999 | Daneshvar ............. | A61B 17/24 128/DIG. 25 |
| 5,915,383 A * | 6/1999 | Pagan ................... | A61M 16/04 128/911 |
| 6,196,225 B1 * | 3/2001 | Allgeyer ............... | A61M 16/04 128/200.26 |
| 6,383,195 B1 * | 5/2002 | Richard ............... | A61B 17/221 606/114 |
| 6,428,506 B1 * | 8/2002 | Simhambhatla ........ | A61L 27/16 428/36.9 |
| 7,425,357 B2 * | 9/2008 | Lim ...................... | A61L 29/085 604/103.05 |
| 10,188,272 B2 * | 1/2019 | Holzer ............... | A61B 1/00151 |
| 2005/0089655 A1 * | 4/2005 | Lim ...................... | A61L 29/085 428/34.1 |
| 2006/0264707 A1 * | 11/2006 | Kinney ................. | A61B 1/005 600/116 |
| 2009/0105543 A1 * | 4/2009 | Miller ................... | A61B 1/126 604/257 |
| 2009/0182278 A1 | 7/2009 | Eversull et al. | |
| 2010/0022832 A1 * | 1/2010 | Makiyama ............. | A61B 1/015 600/115 |
| 2011/0009696 A1 * | 1/2011 | Miyoshi ................... | A61B 1/01 600/114 |
| 2012/0178994 A1 | 7/2012 | Schembre | |
| 2012/0238816 A1 * | 9/2012 | Gunday ............. | A61B 1/00135 600/114 |
| 2013/0023840 A1 * | 1/2013 | Loske .................... | A61B 90/39 604/319 |
| 2013/0116549 A1 | 5/2013 | Gunday et al. | |
| 2014/0066897 A1 * | 3/2014 | Campbell ............. | A61L 29/085 604/509 |
| 2014/0276585 A1 | 9/2014 | Gianotti | |
| 2015/0306361 A1 * | 10/2015 | Feig ........................ | A61M 1/67 604/509 |
| 2015/0351613 A1 * | 12/2015 | Knight .............. | A61M 16/0816 600/114 |
| 2017/0151415 A1 * | 6/2017 | Maeda ................... | A61M 25/09 |
| 2020/0046216 A1 * | 2/2020 | Moein ...................... | A61B 1/32 |

FOREIGN PATENT DOCUMENTS

| | | |
|---|---|---|
| JP | 2010-537736 A | 12/2010 |
| JP | 2012-024358 A | 2/2012 |
| JP | 2012-81130 A | 4/2012 |
| JP | 2014-516293 A | 7/2014 |
| JP | 2016-501622 A | 1/2016 |
| WO | 2019-226814 A1 | 11/2019 |

OTHER PUBLICATIONS

Meseeha M, Attia M. Endoscopic Retrograde Cholangiopancreatography. [Updated Aug. 11, 2020]. In: StatPearls [Internet]. Treasure Island (FL): StatPearls Publishing; Jan. 2021. Available from: https://www.ncbi.nlm.nih.gov/books/NBK493160/.

* cited by examiner

DEVICES, SYSTEMS, AND METHODS FOR AN INSTRUMENT ACCESSORY

PRIORITY

This application claims the benefit of priority under 35 USC § 119 to U.S. Provisional Patent Application Ser. No. 62/969,922, filed Feb. 4, 2020, which is incorporated by reference herein in its entirety and for all purposes.

FIELD

The present disclosure pertains to medical devices. More particularly, the present disclosure pertains to instrument accessory devices and related systems and methods, particularly as may increase the effectiveness and efficiency of duodenoscopy, endoscopy and colonoscopy procedures.

BACKGROUND

Medical devices, for example duodenoscopes, endoscopes, and colonoscopes, are used in medical procedures to examine and treat conditions within the digestive tract. Endoscopic Retrograde Cholangiopancreatography (ERCP) is used to examine and treat issues in the common bile duct and pancreatic ducts. In some procedures, cannulation of the bile duct can difficult, with movement in the duodenum creating positioning and stabilization of the medical device hard to achieve. Peristaltic movements in the duodenum can require medication to the patient to suppress. Further, the tightly contracted musculature of the papilla requires high levels of precision to maneuver the medical device through the papilla opening. Consequently, the effectiveness and efficiency of the procedure may become compromised, and the inability to cannulate the common bile duct may result in a failed ERCP.

It is with the above and other considerations in mind that the improvements of the present disclosure may be useful.

SUMMARY

The present disclosure, in its various aspects, is directed generally to instrument accessory devices, implementation methods, and related systems. Embodiments according to the present disclosure, including those described herein, may increase particularly the effectiveness and efficiency of procedures used for the examination and treatment of conditions within the body, e.g., cannulation of the bile duct during ERCP.

In an aspect, an instrument accessory device may include an expandable member having a proximal end, a distal end, a longitudinal axis, an inner surface, and an outer surface, the outer surface defining an outer diameter. The inner surface may define an instrument lumen extending between the proximal end and the distal end of the expandable member. The instrument lumen may be configured to receive an instrument therethrough. The expandable member may comprise an expandable material. The device may comprise a constrainment element disposed about the outer surface of the expandable member, the constrainment element comprising a proximal end, a distal end, an inner surface, and an outer surface.

In various embodiments described here or otherwise, the expandable material may comprise a sponge. The device may comprise a wire in fluid communication with the proximal end of the outer surface of the constrainment element, wherein the constrainment element comprises irrigation ports. The wire may comprise a fluid lumen (i.e., the wire may be in the form of a tubular member). The inner surface of the constrainment element may comprise irrigation ports. The expandable member may comprise a base and the expandable material may be disposed around the base, the base comprising a proximal end, a distal end, a longitudinal axis, and an instrument lumen extending between the proximal end and the distal end of the base. The expandable material may be adhered to the base. The base may comprise irrigation ports. The instrument lumen may be configured to receive a medical device such as a duodenoscope, an endoscope or a colonoscope. The instrument lumen may be configured to maintain frictional contact with the medical device. When the expandable member is in an expanded condition, the outer diameter may be larger than when the expandable member is in a constrained condition.

In an aspect, a medical system may include an instrument. The system may include an instrument accessory disposable about the instrument. The instrument accessory may comprise an expandable member having a proximal end, a distal end, a longitudinal axis, an inner surface, and an outer surface disposed about the inner surface. The outer surface may define an outer diameter and the inner surface may define an instrument lumen. The instrument lumen may extend between the proximal end and the distal end of the expandable member. The expandable member may comprise an expandable material. A constrainment element may be disposed about the outer surface of the expandable member. The constrainment element may comprise a proximal end, a distal end, an inner surface, and an outer surface. The instrument lumen may be configured to slidingly receive at least a portion of the instrument when the expandable member is in an expanded condition.

In various embodiments described here or otherwise, the instrument accessory device may be configured to maintain frictional contact with the instrument. The expandable member may be electrically or mechanically expandable. In various embodiments, the expandable member may be expandable upon contacting the expandable material with an expansion fluid. The instrument may be a medical device such as a duodenoscope, a colonoscope or an endoscope.

In an aspect, a method of performing a medical procedure may comprise loading an instrument accessory device onto a distal end of an instrument. The instrument accessory device may comprise an expandable member having a proximal end, a distal end, a longitudinal axis, an inner surface, and an outer surface, the outer surface defining an outer diameter, and the inner surface defining an instrument lumen extending between the proximal end and the distal end of the expandable member. The instrument lumen may be configured to receive the instrument therethrough. The expandable member may comprise an expandable material. A constrainment element may be disposed about the outer surface of the expandable member, the constrainment element comprising a proximal end, a distal end, an inner surface, and an outer surface. The instrument may be advanced through the instrument lumen of the instrument accessory device, the instrument accessory device may comprise an expandable member and a constrainment element disposed about the outer surface of the expandable member. The instrument and instrument accessory device may be inserted into a patient. The constrainment element may be removed from around a portion of the expandable member. The expandable member may be expanded.

In various embodiments described here or otherwise, the method may also comprise using the instrument to perform a procedure. The expandable member may be contracted, and the instrument and instrument accessory device may be removed. For example, the constrainment element may be a contractable mesh, whereby contraction of the mesh around the expandable member contracts the expandable member. As another example, the constrainment element may be a sheathing cover, whereby repositioning the expandable member within the sheathing cover contracts the expandable member. The method may further comprise removing the instrument and instrument accessory device. Expanding the expandable member within the patient may comprise expanding the outer diameter. Expanding the expandable member may inhibit movement of the expandable member within the patient. Expanding the expandable member may comprise contacting the expandable member with an expansion fluid. The outer surface may expand to fit a body cavity. The instrument may comprise a medical device such as a duodenoscope, an endoscope or a colonoscope.

In an aspect, a method of performing a medical procedure may comprise loading an instrument accessory device onto a distal end of an instrument. The instrument accessory device may comprise an expandable member having a proximal end, a distal end, a longitudinal axis, an inner surface, and an outer surface, the outer surface defining an outer diameter, and the inner surface defining an instrument lumen extending between the proximal end and the distal end of the expandable member. The instrument lumen may be configured to receive the instrument therethrough. The expandable member may comprise an expandable material. A constrainment element may be disposed about the outer surface of the expandable member, the constrainment element comprising a proximal end, a distal end, an inner surface, and an outer surface. The instrument accessory device may be loaded onto the distal end of the instrument by advancing the instrument through the instrument lumen of the instrument accessory device. The instrument and the instrument accessory device may be inserted into a patient. The constrainment element may be removed from around a portion of the expandable member, and the expandable member may be expanded.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

Figure 1:
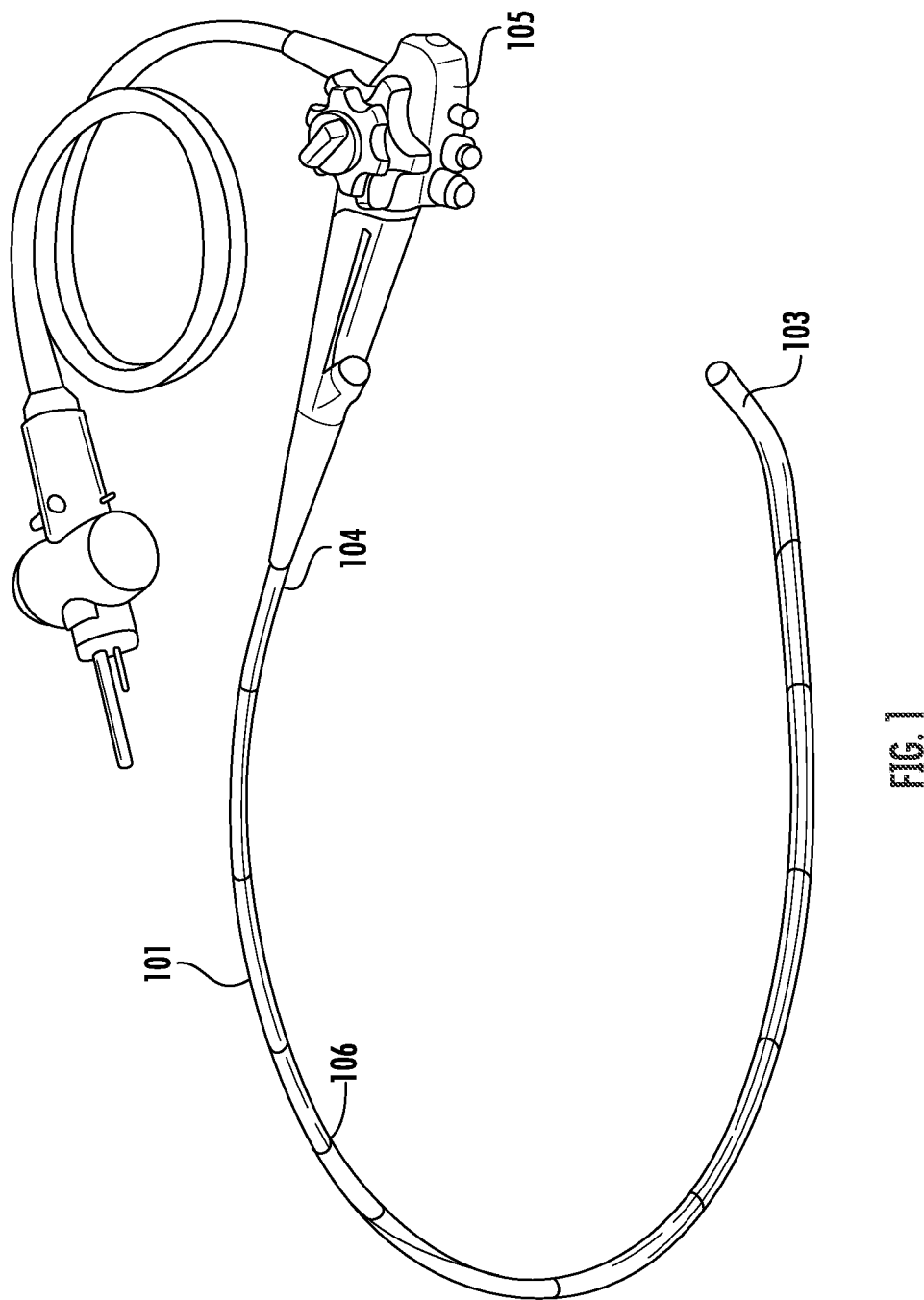
FIG. 1 illustrates an exemplary medical device of a type described in an embodiment of the present disclosure.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Various embodiments according to the present disclosure are described below. As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The detailed description should be read with reference to the drawings, which are not necessarily to scale, which depict illustrative embodiments, and which are not intended to limit the scope of the disclosure.

Embodiments of the present disclosure may include an instrument accessory, as a device for use with an instrument. An instrument may be a medical device such as an endoscope, duodenoscope, a colonoscope or the like. The device may include various components and configurations.

Embodiments of this disclosure may comprise a medical device system. A medical device system may include an instrument, a handle, an instrument accessory, and/or an expansion fluid, or the like. Embodiments of the devices and systems may be used to fill a patient's body lumen around the instrument, during a medical procedure, to inhibit movement of the instrument. Alternatively, embodiments of the devices and systems may be used to fill the patient's body lumen around an instrument, for example, during a colonoscopy, thereby opening folds of the intestine, which can make examination difficult. Various embodiments described herein comprise a device having an expandable member about an instrument lumen that can slidingly receive an instrument extended therethrough. The expandable member once expanded within the body lumen may inhibit movement of the instrument within the body lumen in some embodiments. In some embodiments, the body lumen may include a lumen, organ, vessel, passage, or the like, within, e.g., the digestive system, or the like.

Endoscopic Retrograde Cholangiopancreatography (ERCP) is used to examine and treat issues in the common bile duct and pancreatic ducts. A duodenoscope is introduced into the patient via the mouth, and advanced through the stomach and the small intestine. The duodenoscope may be used to access the ampulla of Vater, which is formed by the union of the pancreatic duct and the common bile duct and is specifically located at the major duodenal papilla, in order to reach the pancreatic and bile ducts. The positioning of the duodenoscope relative to the papilla can influence the success of the procedure, and can be made difficult by movement of the duodenum. The expandable members of the accessory devices of the present disclosure, once expanded within the duodenum, may inhibit movement of the instrument within the duodenum.

Colonoscopies may be used to examine and treat issues in the digestive system, specifically the large intestine. A colonoscope is introduced into the patient via the rectum, through the colon and advanced through the large intestine. The folds of the intestine can make examination difficult, as they may hide polyps or debris. The expandable members of the accessory devices of the present disclosure, once expanded within the intestine, may un-crease the folds thereby improving examination quality.

For various uses of duodenoscopes, endoscopes, colonoscopes, or other instruments, within various body lumens and for various purposes, such as described above, embodiments of the accessory devices, systems and methods of the present disclosure may be utilized to enable the physician to perform procedures with greater precision, accuracy, and ease than without the accessory devices.

An instrument accessory device in accordance with the present disclosure may include an expandable member. An expandable member may include an expandable material such as medical grade collagen, cellulose, silicone or polyurethane, shape memory material which may be in the form of a sponge, foam, a brush, braid or the like. An expandable member may include an inner surface which may correspond to the expandable material or may correspond to a layer of a frictional material such as silicone, or the like. An expandable member may include an outer surface which may correspond to the expandable material or may correspond to an elastic material such as scaffolding, a sponge, a mesh, a braid, or the like or may be a substantially non-expandable material such as a sheathing cover. An expandable member may be mechanically actuated, electrically actuated, pneumatically/hydraulically actuated, inflated, or the like. In various embodiments, the expandable member is expanded by contacting the expandable material with an expansion fluid. An expandable member may transition from a collapsed configuration to an expanded configuration to occlude, stretch, establish patency, or maintain patency of a body lumen.

An instrument accessory device may include a constrainment element. A constrainment element may be a non-elastic material, example, a polyaminde such as Nylon, a fluoropolymer such as polytetrafluoroethylene (PTFE), polyether block amides (e.g., Pebax®), modified poly (ethylene terephthalate) (MPET), or a semi-elastic material such as silicone, polyurethanes, including ChronoFlex® polycarbonate-based thermoplastic urethanes, latex or a braid made form similar materials. In various embodiments, the constrainment element is in the form of sheathing cover which may be advanced over the expandable member and/or into which the expandable member may be drawn.

An instrument accessory device may have a fluid inlet that may extend through the base of the expandable member. The fluid inlet may accept an irrigation fluid for wetting and/or lubricating the expandable member.

In one method of performing an endoscopy, a distal end of a medical device such as a duodenoscope may be advanced through the small intestine via the mouth of a patient. Once inside the patient, the digestive system can be visually examined and the pancreatic and bile ducts may be accessed using an instrument passed through a working channel from a handle at the proximal end of the medical device that remains outside of the body.

Referring to FIG. 1, an embodiment of a medical device of the type described in the present disclosure is illustrated. The medical device 101 is one example of an instrument that can be used with an instrument accessory device described further herein. The medical device 101 comprises a distal end 103 and a proximal end 104 with a lumen or working channel extending therethrough. A handle 105 at the proximal end 104 may be operated by a medical professional to manipulate the medical device 101. The medical device 101 may include cuts or channels 106 along a wall 106 of the insertion portion of the medical device 101 in order to facilitate movement and flexibility within a patient, e.g., by operation of steering knobs at the handle 105.

Figure 2A:
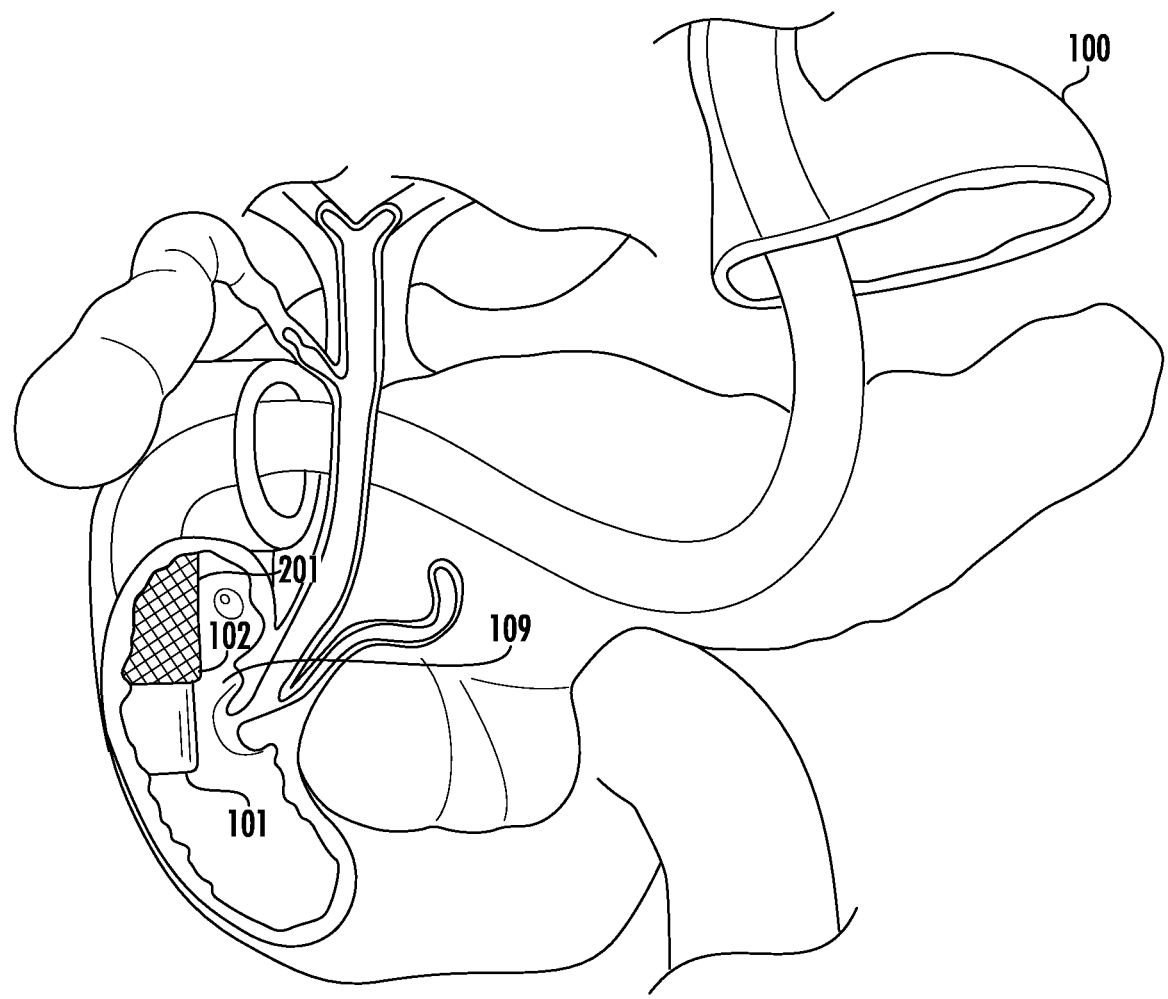
FIG. 2A illustrates a partial cross-sectional view of a medical device system with an instrument accessory device in a collapsed configuration within a body and an exemplary medical device, such as the medical device of FIG. 1, extended therethrough, in accordance with an embodiment of the present disclosure.
Figure 2B:
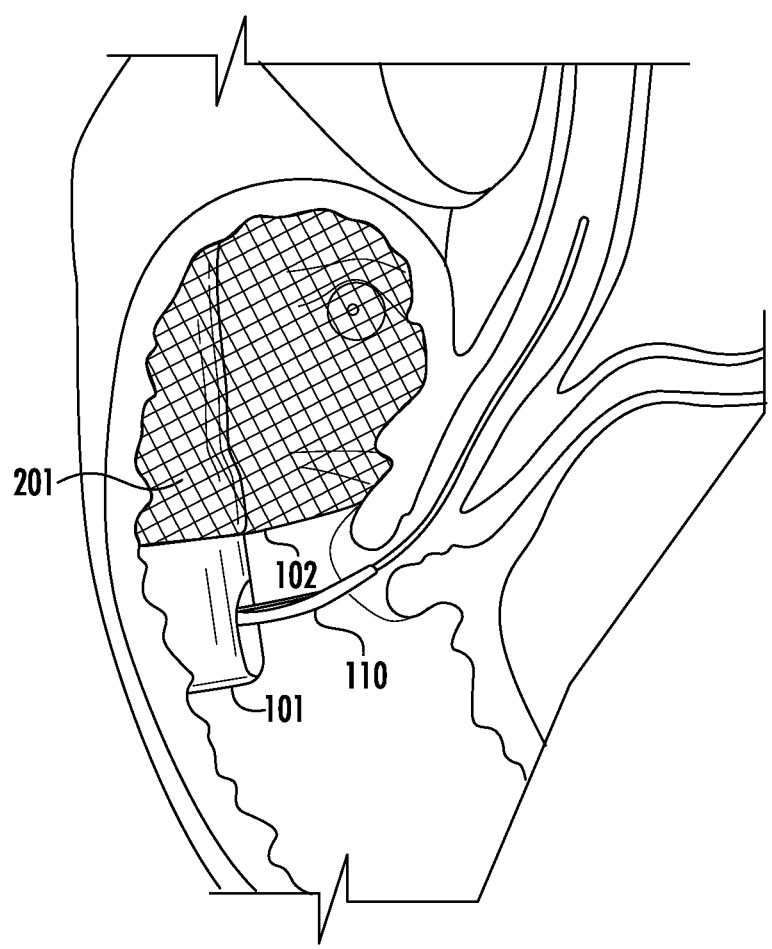
FIG. 2B illustrates a partial cross-sectional view of a medical device system with an instrument accessory device, such as the device of FIG. 2A, in an expanded configuration within a body and an exemplary medical device, such as the medical device of FIG. 1, extended therethrough, in accordance with an embodiment of the present disclosure.

Referring to FIGS. 1, 2A and 2B, a view of a medical device system within the body is illustrated according to an embodiment of the present disclosure, which includes an instrument accessory device 102 slidably disposed around a medical device 101 (e.g., the medical device 101 of FIG. 1). The distal end 103 of the medical device 101 and instrument accessory device 102 may be advanced through the stomach 100, with the proximal end of the medical device 101 remaining outside the body. When advancing the medical device, the instrument accessory device 102 remains disposed about the medical device 101. Once the medical device and instrument accessory device 102 are in position, the expandable member 201 of the instrument accessory device 102 may be expanded (FIG. 2B). The expandable member 201 of the instrument accessory device 102 may substantially dilate a body lumen 109 (FIG. 2A) while in the expanded configuration. The expandable member 201 may be transitioned from a collapsed configuration to an expanded configuration by the removal of the constrainment element. The body lumen 109, e.g., small intestine, duodenum, etc., may be substantially occluded by the expandable member 201 when the expandable member 201 is in an expanded state, as the expandable member 201 may fill the body lumen 109. The contact created between the expandable member 201 and the lumen 109 upon expansion of the expandable member 201 may prevent longitudinal, rotational, and/or translational movement within the body lumen 109. The medical device 101 may be substantially immovable within the instrument lumen within the expandable member 201, for example, allowing the pancreatic and bile ducts may be accessed using an instrument 110 passed through a working channel of the medical device.

Figure 3:
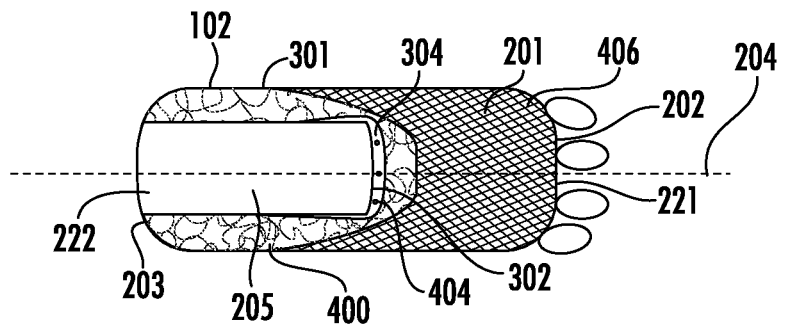
FIG. 3 illustrates a partial cross-sectional view of the instrument accessory device, in accordance with an embodiment of the present disclosure.

Referring to FIG. 3, a partial cross-sectional view of an instrument accessory device 102 is illustrated according to embodiments of the present disclosure. The instrument accessory device 102 includes an expandable member 201 having a proximal end 202, and a distal end 203. An inner surface 302 defines an inner diameter of the expandable member 201, extending between the proximal 202 and distal 203 ends. The inner surface 302 defines an instrument lumen 205 having a longitudinal axis 204, a proximal opening 221 at the proximal end 202, and a distal opening 222 at the distal end 203, with the instrument lumen 205 extending through the instrument accessory device 102. The instrument lumen 205 is configured to receive an instrument, e.g., the medical device of FIG. 1, extendable through the instrument lumen 205. The expandable member 201 having a proximal end 202 and a distal end 203 is illustrated in a collapsed configuration in FIG. 3. An outer surface 301 defining an outer diameter of the expandable member 201 extends between the proximal end 202 and distal end 203 of the expandable member 201 along a length of the longitudinal axis 204 of the instrument lumen 205. The longitudinal axis 204 of the instrument lumen 205 and the longitudinal axis of the expandable member 201 may be coincident with each other, as shown, or may be radially offset from each other. In the embodiment shown, the expandable member 201 comprises a base 304 with a proximal end and a distal end which forms the inner surface 302. The expandable member 201 is supported by the base 304, extending between the distal end 203 and the proximal end 202 of the base 304. The expandable member 201 also comprises an expandable material 400 disposed about the base 304 and an outer structure 406 (i.e., a constrainment element) disposed about the expandable material 400. The base 304 comprises irrigation ports 404 which are connected to a source of fluid. The material at the inner surface 302 may be a material, e.g. silicone, which maintains frictional contact with an instrument within the instrument lumen 204. In this regard, the material at the inner surface 302 may correspond that of the base 304 or may correspond to a coating of material on the base 304. The material of the outer structure 406 may be an expandable material, e.g., a mesh material.

Figure 4A:
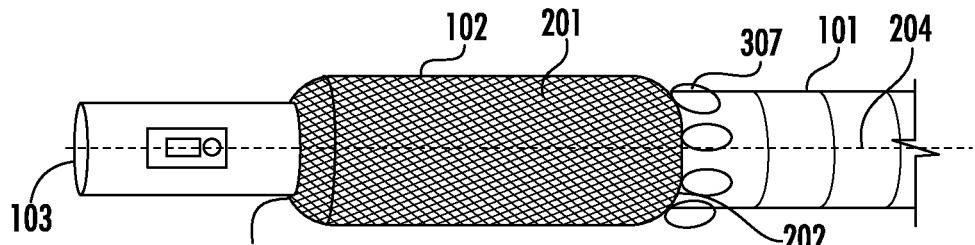
FIG. 4A illustrates a perspective view of an instrument accessory device in a collapsed configuration, in accordance with an embodiment of the present disclosure.
Figure 4B:
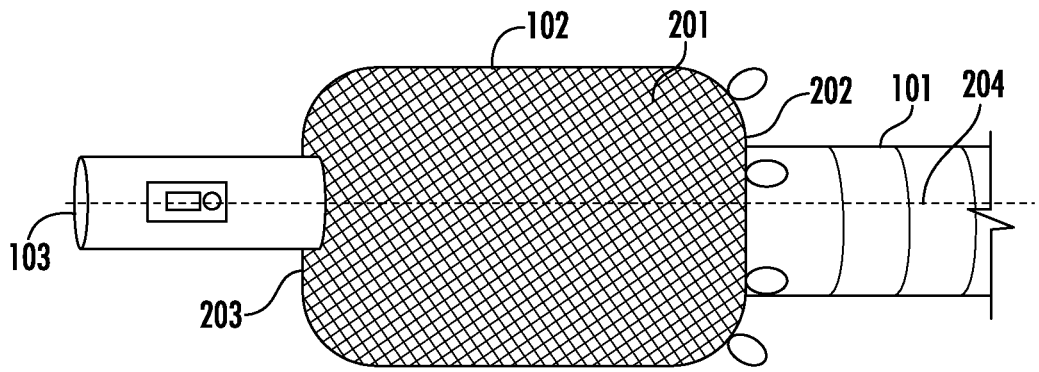
FIG. 4B illustrates a perspective view of the instrument accessory device of FIG. 4A, in an expanded configuration.
Figure 4C:
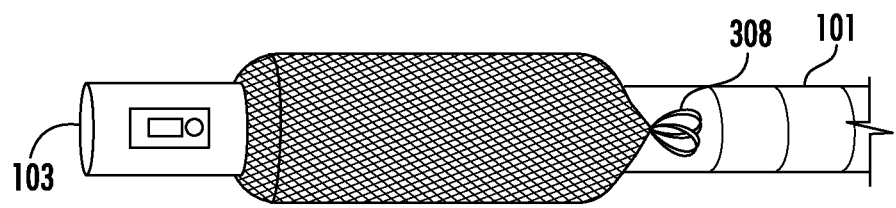
FIG. 4C illustrated a perspective view of an instrument accessory device in a collapsed configuration, in accordance with an embodiment of the present disclosure.
Figure 5A:
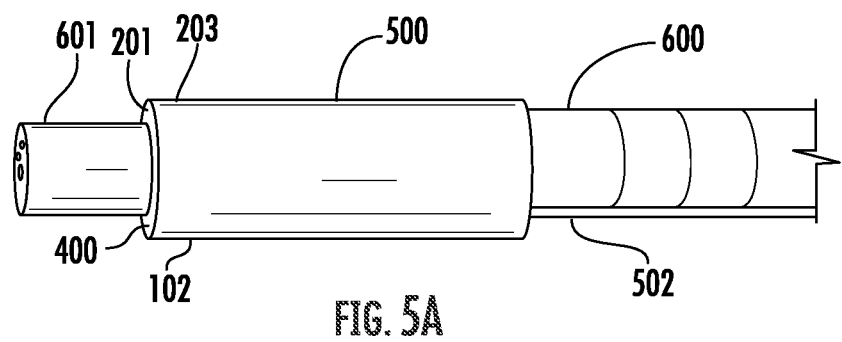
FIG. 5A illustrates a perspective view of a colonoscope system in a collapsed configuration, in accordance with an embodiment of the present disclosure.
Figure 5B:
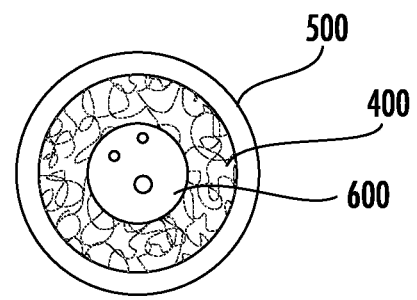
FIG. 5B illustrates a partial cross-sectional view of the colonoscope system of FIG. 5A in the collapsed configuration.
Figure 6A:
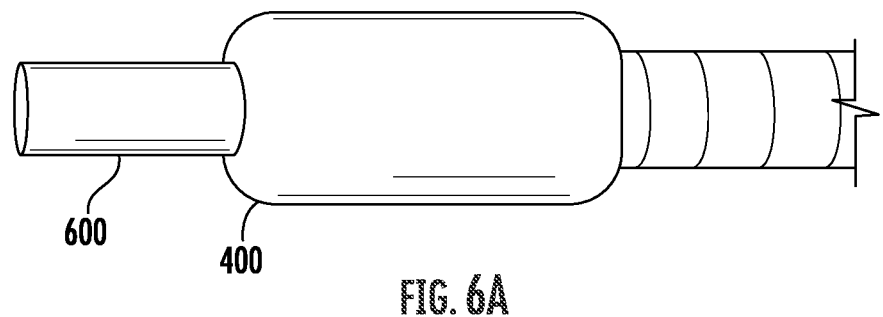
FIG. 6A illustrates a perspective view of a colonoscope system in an expanded configuration, in accordance with an embodiment of the present disclosure.
Figure 6B:
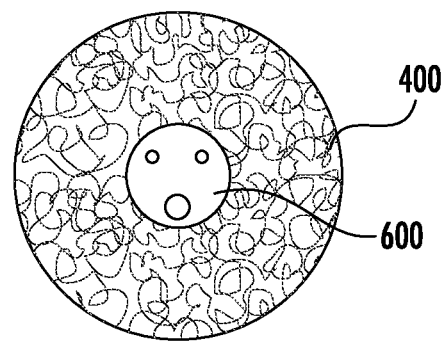
FIG. 6B illustrated a partial cross-sectional view of the colonoscope system of FIG. 6A in the expanded configuration.

Referring to FIGS. 3, 4A, 4B, and 4C an instrument accessory device 102 is illustrated according to embodiments of the present disclosure. The instrument accessory device 102 includes an expandable member 201 having a proximal end 202, a distal end 203, and an instrument lumen 205 therethrough. The instrument accessory device 102 of FIG. 4A is in a collapsed configuration. A number of loops 307 are disposed at the proximal end 202 of the expandable member 201. In a collapsed configuration, these loops 307 may be held by an accessory. The removal of this accessory would allow for the expanded configuration of FIG. 4B. To further expand the expandable member 201, fluid may be injected into the expandable member 102 through the irrigation ports 404 of the base 304 of FIG. 3 such that the fluid contacts and expands the expandable material 400 of the expandable member 102. The instrument accessory device 102 of FIG. 4C is in a collapsed configuration. In this embodiment, the loops 308 are held together until released for the expansion of the expandable member 201. The expandable member 201 is collapsed when the outer structure 406 is constrained. The base 304 is adhered to the outer structure 406 along the length of the expandable member 201. The adhered surfaces may be achieved by an adhesive, flowed material, welding (e.g., laser, ultrasonic, hot jaw thermal, etc.), melt/re-melt flow processes, or the like. The adhered surfaces create a substantially tight fluid seal between the base 304 and the outer structure 406 such that an expansion fluid may be supplied through a fluid lumen to transition the expandable member 201 between the collapsed configuration of FIG. 4A and an expanded configuration of FIG. 4B. The expandable member 201 in the expanded configuration is illustrated in a rounded cylindrical shape, but the expandable member 201 may be other shapes such as, e.g., a spheroid, a torus, a combination thereof, or the like. A medical device extending through the instrument lumen 205 of the expandable member 201 may be used to examine a body lumen, as the inner surface 302 remains in frictional contact with the medical device when the expandable member 201 is collapsed. With the expandable member 201 in the expanded configuration in a body lumen, the medical device is held in place within the body lumen, as the expandable member expands to the diameter of the body lumen.

The instrument accessory device 102 is illustrated in FIGS. 3 and 4A-C such that it is configured to receive a medical device 101 through the proximal end 202 toward the distal end 203.

Referring to FIGS. 5A, 5B, 6A and 6B, the instrument accessory device 102 is illustrated in a collapsed configuration as part of a colonoscope system that includes a colonoscope 600 according to an embodiment of the present disclosure. A constrainment element 500 surrounds the expandable material 400 of the expandable member. By retracting the constrainment element 500, the expandable material 400 of the expandable member is allowed to expand. In some embodiments the outer structure 500 corresponds to a retractable sheathing cover. The constrainment element 500 may be a non-elastic material, e.g., Nylon, PTFE, Pebax®, MPET. The instrument accessory device 102 depicted in FIGS. 5A, 5B, 6A and 6B is shown at the distal end 601 of the colonoscope 600, including the expandable member 201. The expandable member 201 is frictionally disposed about the colonoscope 600. The distal end 601 of the colonoscope 600 extends further than the distal end 203 of the instrument accessory device 102. A wire 502 having a fluid lumen is disposed on the proximate end 501 of the constrainment element 500, which is provided with irrigation ports on its inner surface.

In various embodiments, an expandable member may have an expanded configuration and a collapsed configuration. An expandable member may comprise an outer surface formed of an outer surface material and an inner surface formed of an inner surface material. The outer surface material may comprise a variety of compliant, semi-compliant, or non-compliant materials. These materials may comprise silicone, latex, polyurethane, rubber, isobutylene or the like. The thickness of a wall of the outer surface material may vary with the material and may relate to the outer diameter of the outer surface in the collapsed and the expanded configuration. The inner surface material may comprise a variety of compliant, semi-compliant, or non-compliant materials. These materials may comprise silicone, latex, polyurethane, rubber, isobutylene or the like. The thickness of a wall of the inner surface may vary with the material and may relate to the inner diameter of the inner surface in the collapsed and the expanded configuration. An expandable member may be expanded and collapsed or otherwise stretched once or a plurality of times to increase its elasticity prior to use within a patient, which may improve a symmetrical expansion of the expandable member and may improve the centering mechanics of the expandable member. An expandable member may be expanded via a supply of an expansion fluid through one or more irrigation ports. The same irrigation ports may be used to expand the expandable member.

As previously indicated, the inner and outer surfaces of the expandable member may comprise a polymeric material. When the expandable member is expanded, the inner surface may crimp an instrument in place and not allow the instrument to move within the instrument lumen.

In various embodiments, the instrument accessory device may be disposable. In alternate embodiments, the instrument accessory device may be reusable.

In various embodiments, an expansion fluid supplied through an elongated delivery member may include saline, water, dilute contrast media, or the like.

In various embodiments, a method of performing a medical procedure may include placing the instrument accessory on the distal end of an instrument. The instrument is advanced through the instrument lumen while the expandable member is in a collapsed state. The expandable member is disposed about the instrument and configured to maintain frictional contact with the instrument. The instrument and instrument accessory device are together inserted into a patient. The expandable member can be expanded within the patient, dilating the patient's body lumen, e.g., the colon, the intestines, or the like. The expandable member increases in diameter when the expandable member is expanded, allowing the instrument to remain in a stable position within the body lumen. While the expandable member is expanded, procedures such as ERCP may be performed. After the procedure, the expandable member is then contracted (e.g., by repositioning the expandable member within a constrainment element), and the instrument and instrument accessory device removed from the patient. Expanding the expandable member and stabilizing the instrument allows for precise movements of a catheter from within the instrument. This can occur due to the outer diameter dilating the body lumen, preventing movement of the device. The instrument may be any device used to perform the procedure, e.g., a medical device such as a duodenoscope, endoscope, colonoscope, or the like.

In various embodiments, a method of performing a colonoscopy may include placing the instrument accessory on the distal end of an instrument. The instrument is advanced through the instrument lumen while the expandable member is in a collapsed state. The expandable member is disposed about the instrument and configured to maintain frictional contact with the instrument. The instrument and instrument accessory device are together inserted into a patient. The expandable member can be expanded within the patient, dilating the patient's body lumen, e.g., the colon, the intestines, or the like. The expandable member may remain expanded while the instrument and instrument accessory device is removed from the patient. This can allow the expandable member to disturb folds and crevices for investigation by the colonoscope.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. An instrument accessory device, comprising:
an expandable member having a proximal end, a distal end, a longitudinal axis, an inner surface, and an outer surface, the outer surface defining an outer-most diameter of the expandable member, and the inner surface defining an instrument lumen extending between the proximal end and the distal end of the expandable member, the instrument lumen configured to receive an instrument therethrough such that the inner surface contacts the instrument, wherein the expandable member comprises an expandable material; and
an expandable and contractible constrainment element disposed about the outer surface of the expandable member, the constrainment element comprising: a proximal end, a distal end, an inner surface in contact with the outer surface of the expandable member, and an outer surface;
wherein the constrainment element is configured to be adjusted relative to the expandable member to cause contraction of the expandable member; and
wherein the constrainment element comprises an expandable and contractible mesh.

2. The device of claim 1, wherein the expandable material comprises a sponge.

3. The device of claim 1, further comprising a wire in fluid communication with the proximal end of the outer surface of the constrainment element, wherein the constrainment element comprises irrigation ports.

4. The device of claim 3, wherein the wire further comprises a fluid lumen.

5. The device of claim 1, wherein the expandable member comprises a base and the expandable material is disposed around the base, the base comprising a proximal end, a distal end, a longitudinal axis, and an instrument lumen extending between the proximal end and the distal end of the base.

6. The device of claim 5, wherein the expandable material is adhered to the base.

7. The device of claim 5, wherein the base comprises irrigation ports.

8. The device of claim 1, wherein the instrument lumen is configured to receive a duodenoscope, an endoscope or colonoscope.

9. The device of claim 8, wherein the instrument lumen is configured to maintain frictional contact with the duodenoscope, endoscope or colonoscope.

10. The device of claim 1, wherein when the expandable member is in an expanded condition, an outer diameter of the expandable member is larger than when the expandable member is in a constrained condition.

11. A medical system, comprising:
an instrument; and
an instrument accessory device disposable about the instrument, comprising:
an expandable member having a proximal end, a distal end, a longitudinal axis, an inner surface, and an outer surface, the outer surface defining an outer-most diameter of the expandable member, and the inner surface defining an instrument lumen extending between the proximal end and the distal end of the expandable member, wherein the expandable member comprises an expandable material; and
an expandable and contractible constrainment element disposed about the outer surface of the expandable member, the constrainment element comprising: a proximal end, a distal end, an inner surface in contact with the outer surface of the expandable member, and an outer surface;

wherein the constrainment element is configured to be adjusted relative to the expandable member to cause contraction of the expandable member;

wherein the instrument lumen is configured to slidingly receive at least a portion of the instrument such that the inner surface of the expandable member contacts the instrument; and wherein the constrainment element comprises an expandable and contractible mesh.

12. The system of claim 11, wherein the instrument accessory device is configured to maintain frictional contact with the instrument.

13. The system of claim 11, wherein the expandable material is expandable upon contact with an expansion fluid.

14. The system of claim 11, wherein the instrument is a duodenoscope, a colonoscope or an endoscope.

15. The device of claim 1, wherein the constrainment element comprises a plurality of loops configured to be engaged to cause contraction of the expandable member.

\* \* \* \* \*